US007767073B2

(12) United States Patent
Callens et al.

(10) Patent No.: US 7,767,073 B2
(45) Date of Patent: Aug. 3, 2010

(54) ORGANIC SALTS AND THEIR USE AS REAGENTS IN ELECTROCHEMICAL REACTIONS

(75) Inventors: Roland Callens, Grimbergen (BE);
Frank Becu, Zwevezele-Wingene (BE);
Frans Borremans, Destelbergen (BE);
Franky Fant, Wetteren (BE)

(73) Assignee: Solvay S.A. (BE)

( * ) Notice: Subject to any disclaimer, the term of this patent is extended or adjusted under 35 U.S.C. 154(b) by 1211 days.

(21) Appl. No.: 10/527,342

(22) PCT Filed: Sep. 10, 2003

(86) PCT No.: PCT/EP03/10187

§ 371 (c)(1),
(2), (4) Date: Sep. 12, 2005

(87) PCT Pub. No.: WO2004/024991

PCT Pub. Date: Mar. 25, 2004

(65) Prior Publication Data

US 2006/0049061 A1    Mar. 9, 2006

(30) Foreign Application Priority Data

Sep. 10, 2002  (BE) ................................ 2002/0531
Sep. 11, 2002  (FR) ................................. 02 11404

(51) Int. Cl.
*C25B 3/00* (2006.01)
*C25B 3/06* (2006.01)
*C25B 3/08* (2006.01)

(52) U.S. Cl. ................ 205/413; 205/422; 205/423; 205/431; 205/436; 205/444; 205/455; 205/459; 205/460

(58) Field of Classification Search ................ 205/413, 205/423, 431, 422, 436, 444, 455, 459, 460
See application file for complete search history.

(56) References Cited

U.S. PATENT DOCUMENTS 2,680,713 A * 6/1954 Lindsey, Jr. et al. .......... 205/441
4,824,532 A * 4/1989 Moingeon et al. ........... 205/422
4,931,155 A * 6/1990 Dutcher et al. .............. 205/431
6,663,764 B2 * 12/2003 Thurmuller et al. ......... 205/435

FOREIGN PATENT DOCUMENTS

DE    28 42 760     4/1980
EP    1 247 880    10/2002

OTHER PUBLICATIONS

Moeller et al., "Anodic Amide Oxidations in the Presence of Electron-Rich Phenyl Rings: Evidence for an Intramolecular Electron-Transfer Mechanism", J. Org, Chem. (1991), vol. 56, pp. 1058-1067.*

Schlumbach, "Über das Tetraäthylammonium", *Chemische Berichte*, vol. 53, pp. 1689-1693 (1920). (See *Chemical Abstracts*, vol. 15, p. 846 (attached)).
Horner et al., "Hydrogen Transfer. IV. Reductive fission of quaternary ammonium salts at a lead or mercury cathode", *Justus Liebigs Annalen Der Chemie*, vol. 646, pp. 49-64, tables 1-4 (1961). (See abstract).
Koizumi et al., "Reaction Mechanism of Cathodic Crossed Coupling of Acetone with Unsaturated Compounds in Acidic Solution", *Bull. Chem. Soc. Jpn.*, vol. 59, pp. 757-762 (1986).
Médebielle et al., "A New Convenient Synthesis of 5-Aryl Uracils Using $^SRN^1$ Aromatic Nucleophilic Substitution", *Tetrahedron Letters*, vol. 34, No. 21, pp. 3409-3412 (1993).
Kageyama et al., "Electrolytic Preparation Of Tetraalkylammonium Bromites From The Corresponding Bromides", *Chemistry Letters*, pp. 671-672 (1980).
Horner et al., "Hydrogen transfer. 23. Modelling of the mode of action of conducting salts in electrochemical reduction", *Tetrahedron Letters*, No. 32, pp. 2803-2806 (1970). (See abstract).
Ekambaram et al., "The Action of Bases on 1-Mercaptopropyltrimethylammonium Iodide", *Journal Of Organic Chemistry*, vol. 32, pp. 2985-2987 (1967).
Renshaw et al., "Basis for the Physiological Activity Of Onium Compounds", *Journal of Biological Chemistry*, vol. 103, No. 1, pp. 183-186, (p. 185, table 1) (1993).
Lacefield, "Synthesis of an Allylic Alcohol and Chloride in the Nortriptyline Series", *Journal of Medicinal Chemistry*, vol. 14, No. 1, pp. 82-83 (1971).
Shono et al., "Electroorganic Chemistry. 81. Anodic Oxidation of Sulfonamides and Amidophosphates", *J. Org. Chem.*, vol. 49, pp. 3711-3716 (1984).
Shono et al., "Electroorganic Chemistry. 46. A New Carbon-Carbon Bond Forming Reaction at the α-Position of Amines Utilizing Anodic Oxidation as a Key Step", *J. Am. Chem. Soc.*, vol. 103, pp. 1172-1176 (1981).
Rucka et al., "New biocides for cooling water treatment. I. Selected quarternary ammonium salts", *Environment Protection Engineering*, vol. 6, No. 4, pp. 455-464 (1981). (See abstract attached).
Jończyk et al., "Base-mediated Reaction of Quaternary Ammonium Salts with Nitroarenes—Their Useful Functionalization via Vicarious Nucleophilic Substitution (VNS)", *Synthesis*, No. 5, pp. 674-680 (2002).

* cited by examiner

*Primary Examiner*—Edna Wong
(74) *Attorney, Agent, or Firm*—Connolly Bove Lodge & Hutz LLP

(57) ABSTRACT

Use of an organic compound salt of general formula

A-XY    (I)

wherein A means an organic residue, X means a charged group and Y means a counter-ion, as a reagent in an electrochemical reaction and organic compound salt corresponding to the formula

R1R2ZC-T-Q-XY wherein
X is a charged group,
Y is a counter-ion,
Z is a group capable of being substituted,
R1 and R2 mean organic residues,
T means a group containing a hetero atom selected among N-R4, O and S, and
Q means a connecting group linking the hetero atom and the charged group.

14 Claims, No Drawings

ORGANIC SALTS AND THEIR USE AS REAGENTS IN ELECTROCHEMICAL REACTIONS

RELATED APPLICATIONS

This application is a national stage application (under 35 U.S.C. 371) of PCT/EP2003/010187 filed Sep. 10, 2003 which claims benefit to Belgian application 2002/0531 filed Sep. 10, 2002 and French application 0211404 filed Sep. 11, 2002.

The present invention concerns the use of organic compounds as reagents in electrochemical reactions and a process for producing an organic substance comprising an electrochemical reaction stage.

Electrochemical reactions are used industrially for producing certain commodities such as for example adiponitrile, certain fine chemical substances such as anisaldehyde or anthraquinone and certain specialities such as cysteine or picolinic acid.

Technical criteria important for the economics of such processes include, among others, a high chemical yield, a high electrochemical yield, low energy consumption, a high concentration of the starting substances in the electrochemical reaction medium, good electrode stability, long membrane life, ease of isolation of the product and the possibility of recycling the electrolyte comprising solvent and a conducting salt.

The patent application DE-2842760 describes the methylation of N-alkylated urethanes in the α position by electrochemical oxidation in methanolic solution in the presence of a conducting salt.

It was desirable to find an electrochemical reaction usable in the production of substances and to a maximal extent meeting the aforesaid criteria.

The invention thus concerns the use of an organic compound salt of general formula $$A\text{-}XY \qquad (I)$$

wherein A means an organic residue, X means a charged group and Y means a counter-ion, as a reagent in an electrochemical reaction.

Surprisingly, it has been found that the use according to the invention makes it possible to improve the efficiency of electrochemical reactions, in particular as regards their chemical and electrochemical yield and their energy consumption. The use according to the invention makes it possible to carry out electrochemical reactions in a medium having a high concentration of reactant. The use according to the invention ensures good conductivity of the reaction medium for the electrochemical reaction. The electrochemical reaction can be effected in the substantial absence of conducting salts. The isolation of the product can be easily effected, the latter often appearing in a crystallisable form.

"Reagent" is intended to mean a compound which is used as such in the reaction. This is different from the formation of charged species which could take place in the course of an electrochemical reaction from organic compounds other than salts.

"Electrochemical reaction" is intended to mean in particular a reaction comprising an electron transfer between the organic compound salt and an electrode and the formation or cleavage of at least one covalent bond of the organic compound salt which has undergone the electron transfer. Typical reactions include the formation of a C—H bond, of a C—C bond or of a C-hetero atom bond. The formation of C—O bonds is preferred.

In the organic compound salt, the group A is an organic residue.

"Organic residue" is intended to mean any group which can contain linear or branched alkyl or alkylene groups, which may include hetero atoms such as in particular atoms of boron, silicon, nitrogen, oxygen and sulphur. It can also contain cycloalkyl or cycloalkylene groups, heterocycles and aromatic systems. The organic residue can contain double or triple bonds and functional groups.

The organic residue contains at least 1 carbon atom. Often, it contains at least 2 carbon atoms. Preferably, it contains at least 3 carbon atoms. More particularly preferably, it contains at least 5 carbon atoms.

The organic residue generally contains at most 100 carbon atoms. Often, it contains at most 50 carbon atoms. Preferably, it contains at most 40 carbon atoms. More particularly preferably, it contains at most 30 carbon atoms.

"Alkyl group" is intended to mean in particular a linear or branched alkyl substituent containing from 1 to 20 carbon atoms, preferably 1, 2, 3, 4, 5, 6, 7, 8, 9 or 10 carbon atoms. Specific examples of such substituents are methyl, ethyl, n-propyl, isopropyl, n-butyl, isobutyl, tert-butyl, n-pentyl, isopentyl, n-hexyl, 2-hexyl, n-heptyl, n-octyl and benzyl.

"Cycloalkyl group" is intended to mean in particular a substituent containing at least one saturated carbon ring with 3 to 10 carbon atoms, preferably 5, 6 or 7 carbon atoms. Specific examples of such substituents are cyclopropyl, cyclobutyl, cyclopentyl, cyclohexyl and cycloheptyl.

"Alkylene group" or "cycloalkylene group" are intended to mean in particular bivalent radicals derived from alkyl groups or cycloalkyl groups as defined above.

When the organic residue contains one or possibly several double bonds, it is often selected among an alkenyl or cycloalkenyl group containing from 2 to 20 carbon atoms, preferably 2, 3, 4, 5, 6, 7, 8, 9 or 10 carbon atoms. Specific examples of such groups are vinyl, 1-allyl, 2-allyl, n-but-2-enyl, isobutenyl, 1,3-butadienyl, cyclopentenyl, cyclohexenyl and styryl.

When the organic residue contains one or possibly several triple bonds, it is often selected among an alkynyl group containing from 2 to 20 carbon atoms, preferably 2, 3, 4, 5, 6, 7, 8, 9 or 10 carbon atoms. Specific examples of such groups are ethynyl, 1-propynyl, 2-propynyl, n-but-2-ynyl and 2-phenylethynyl.

When the organic residue contains one or possibly several aromatic systems, it is often an aryl group containing from 6 to 24 carbon atoms, preferably from 6 to 12 carbon atoms. Specific examples of such groups are phenyl, 1-tolyl, 2-tolyl, 3-tolyl, xylyl, 1-naphthyl and 2-naphthyl.

"Heterocycle" is intended to mean in particular a cyclic system containing at least one saturated or unsaturated ring formed of 3, 4, 5, 6, 7 or 8 atoms of which at least one is a hetero atom. The hetero atom is often selected among B, N, O, Si, P and S. More often, it is selected among N, O and S.

The heterocycle often corresponds to the formula $$(II)$$

wherein J and L are independently selected among C, N, O and S and m and n independently have values from 0 to 4, preferably 1, 2 or 3.

Specific examples of such heterocycles are aziridine, azetidine, pyrrolidine, piperidine, morpholine, 1,2,3,4-tetrahydroquinoline, 1,2,3,4-tetrahydroisoquinoline, perhydroquinoline, perhydroisoquinoline, (1H)-indole, isoxazolidine, pyrazoline, imidazoline, thiazoline, furan, tetrahydrofuran, thiophen, tetrahydrothiophen, pyran, tetrahydropyran and dioxan.

The organic residues as defined above can be unsubstituted or substituted with functional groups. Functional group is intended to mean in particular a substituent containing or consisting of a hetero atom. The hetero atom is often selected among B, N, O, Al, Si, P, S, Sn, As and Se and the halogens. More often, it is selected among N, O, S and P, in particular N, O and S.

The functional group generally contains 1, 2, 3, 4, 5 or 6 atoms.

As functional groups, for example halogens, a hydroxy group, an alkoxy group, a mercapto group, an amino group, a nitro group, a carbonyl group, an acyl group, an optionally esterified carboxyl group, a carboxamide group, a urea group, a urethane group and the thiolated derivatives of the groups containing a carbonyl group mentioned above, a phosphine, phosphonate or phosphate group, a sulphoxide group, a sulphone group and a sulphonate group may be cited.

In particular, the group A can also form a cyclic system with the group X. A group A containing atoms of nitrogen and/or of oxygen, and in particular heterocycles containing these atoms, is preferred. The group A is generally an organic residue containing at least one atom activated for an electrochemical reaction.

In the organic compound salt, the group X is a cationic or anionic group. A cationic group is preferred.

The group X often contains at least one atom from groups 13, 15 or 16 of the periodic table of the elements. A group X containing at least one atom from groups 13 or 15 of the periodic table of the elements is preferred. Among these atoms, those of the second and third period are more particularly preferred. A group X containing at least one atom of nitrogen or of sulphur is quite particularly preferred.

In a first specific aspect, the group X corresponds to the formula N—C(=NH)—NH$_2^+$. Specific examples of organic compound salts containing this group are selected among the derivatives of arginine, in particular the N$^\alpha$-protected amides of arginine, for example with a heterocycle containing nitrogen as defined above.

In a second specific aspect, the group X corresponds to the formula SR$_2^+$ in which R signifies organic residues, in particular as defined above, it being understood that these residues can be identical or different or form a ring between themselves or with the group A. Particularly suitable as R are alkyl, cycloalkyl or aryl groups such as defined above and more particularly a methyl group. Specific examples of organic compound salts containing this group are selected among the derivatives of S-alkylmethionine, in particular the N$^\alpha$-protected amides of S-methyl-methionine, possibly enantiomerically pure, for example with a heterocycle containing nitrogen as defined above.

When the group X is a cationic group, it preferably corresponds to the formula —NR$_3^+$, in which R is one or several organic residues, in particular as defined above, it being understood that these residues can be identical or different or form a ring between themselves or with the group A. Particularly suitable as R are alkyl, cycloalkyl or aryl groups or groups forming a heterocycle with nitrogen, as defined above.

Alkyl groups and groups forming a heterocycle with nitrogen are more particularly preferred.

Among the trialkylamino groups, the trimethylamino, triethylamino, diethylmethylamino and diethylisopropylamino groups are preferred.

Among the groups forming a heterocycle with nitrogen, those corresponding to the above formula (II) containing a nitrogen atom bearing an alkyl group as defined above, in particular selected among methyl and ethyl, are preferred.

Among the groups forming a ring with the group A, we may cite in particular those corresponding to the formula

(III)

wherein R is as defined above, m is 0, 1, 2 or 3, n is 1 or 2, L is selected among C, O, S and N and A' is a part of the residue A.

The above groups of formula —NR$_3^+$ can be obtained for example from trisubstituted amines by reaction with a precursor containing a group capable of being replaced by nucleophilic substitution, such as Cl.

In the organic chemical salt, the group Y is generally an external counter-ion, that is to say it is not linked by a covalent bond to the group A-X.

The group Y is at least one cation or at least one anion having the polarity opposite to that of the group X. An anionic group is preferred. Monovalent anions are particularly preferred.

As anions, in particular the halogens, complex inorganic anions such as polyfluorinated or polyoxo anions, and organic anions such as in particular the organic sulphonates may be cited. The group Y can be selected, preferably among Br$^-$, Cl$^-$, ClO$_4^-$, BF$_4^-$, PF$_6^-$, toluene-sulphonate (Tos$^-$) and benzenesulphonate (PhSO3$^-$). A group Y selected among Cl$^-$, ClO$_4^-$, BF$_4^-$ and PF$_6^-$ is particularly preferred.

As cations, in particular inorganic or organic cations can be cited. An organic cation is preferred. A tetraalkylammonium cation, such as tetraethylammonium or tetra(n-butyl)ammonium is particularly preferred.

In a first mode of use according to the invention, the group Y comprises at least one anion or at least one cation, in particular monovalent, which is inert under the conditions of the electrochemical reaction. Among the anions which are generally stable under the conditions of the electrochemical reaction, in particular the complex inorganic anions such as polyfluorinated or polyoxo anions, and organic anions such as in particular organic sulphonates may be cited. The anions BF$_4^-$, PF$_6^-$, toluenesulphonate (Tos$^-$) and benzenesulphonate (PhSO3$^-$) are preferred. As cations, the tetraalkylammonium cations cited above are very suitable.

In this mode, the content of inert anion or cation is generally greater than or equal to 50% by weight of the total weight of the group Y. This content is often greater than or equal to 75% by weight of the total weight of the group Y. This is content is preferably greater than or equal to 90% by weight of the total weight of the group Y. In this mode, the group Y can consist essentially of one inert anion or of one inert cation.

It has been found that this mode makes it possible to obtain particularly good electrochemical and chemical yields and makes it possible to attain a particularly high concentration of organic compound salt in organic solvents.

In a particular aspect, the content of inert anion or cation is less than or equal to 99.5% by weight of the total weight of the group Y. In this aspect, the content of inert anion or cation is preferably less than or equal to 97% by weight of the total weight of the group Y. In this particular aspect, the residual part of the group Y advantageously consists of at least one anion or at least one cation capable of being converted into a reactive species under the conditions of the electrochemical reaction. Examples of such anions are the halogens, especially $Br^-$ and $Cl^-$ and in particular $Cl^-$.

Preferably, the group Y is a mixture consisting essentially on the one hand of at least one ion selected among $ClO_4^-$, $BF_4^-$, $PF_6^-$, $Tos^-$ and $PhSO3^-$ and on the other hand of $Cl^-$.

This particular aspect makes it possible to improve the selectivity and productivity of indirect electrochemical reactions in which an active species such as a means of oxidation or of reduction, capable of re acting with an organic compound, is generated in situ by the electrochemical route. This aspect also makes it possible to work in the absence of supplementary quantities of anion or of cation capable of being converted into a reactive species, extrinsic to the group Y of the organic compound salt.

The invention also concerns the organic compound salt corresponding to the first mode of use according to the invention and to this particular aspect.

In a second mode of use according to the invention, the organic compound salt corresponds to the formula

R1R2R3C-T-Q-XY     (IV)

wherein

R1R2R3C means a substituted carbon atom, capable of reacting in the electrochemical reaction, T means an activating group for the electrochemical reaction and Q means a connecting group linking the activating group T and the charged group X.

In the group R1R2R3C, R1 and R2 independently signify hydrogen atoms, organic residues as defined above or R1 and R2 together form organic residues as defined above. At least one of R1 or R2 can form a ring with the group X, the group Q or the group T.

The group R3 is a group capable of being modified in the course of the electrochemical reaction. R3 can for example signify a double bond formed with the group T or one of the groups R1 or R2. R3 is preferably selected among —COOH and a hydrogen atom. A hydrogen atom is more particularly preferred.

The activating group T is generally a hetero atom, as described above in the context of the description of the functional groups. The group T is preferably selected among NR4, O and S. An NR4 group is quite particularly preferred.

R4 means a hydrogen atom or an organic residue as defined above. R4 can form a ring with the substituent R1 or R2. Preferably, R4 is selected among an alkyl or cycloalkyl group as defined above. Particularly preferably, R4 with R1 or R2 forms a heterocycle corresponding to the formula above.

The connecting group Q is generally selected among a linear or branched alkylene or cyclo-alkene group as defined above, preferably containing from 1 to 12 carbon atoms, possibly substituted with a functional group as described above.

Preferably, the group Q is a possibly substituted polymethylene group containing 1, 2, 3, 4, 5, 6, 7 or 8 carbon atoms. Such a group containing 1, 2, 3 or 4 carbon atoms is quite particularly preferred.

The group Q preferably contains a functional group such as described above which links it to the group T. It has been found that the presence of a functional group linking the group Q to the group T is particularly useful when it is desired to carry out subsequent reactions with the product from the electrochemical reaction, for example with the aim of separating the charged group from it. The functional group can also exert a supplementary activating effect and a stabilising effect in the course of the electrochemical reaction.

Specific examples of functional groups linking the group Q to the group T are selected among —(C═O)—, —N—(C═O)—, —O—(C═O)—, —(S═O)—, —N—(S═O)—, —SO$_2$—, —N—SO$_2$—, —(C═S)— and —N—(C═S)—. A functional group selected among —(C═O)—, —N—(C═O)—, —O—(C═O)— and —SO$_2$— is preferred. A functional group selected among —(C═O)— and —SO$_2$— is quite particularly preferred. It is intended to mean that the bond on the right hand side of the functional groups as indicated above is linked to the group T.

In a particularly preferred implementation mode, the organic compound salt corresponds to the formula

R1R2R3C—NR4-Q-NR$_3^+$Y$^-$,     (V)

the substituents being defined above. Particularly preferred examples of the organic compound salt correspond to the following formulae in which the substituents are as defined above:

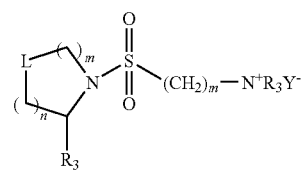

VI

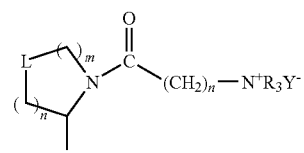

VII

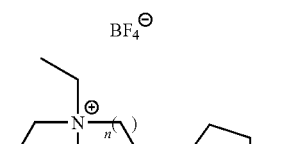

VIII

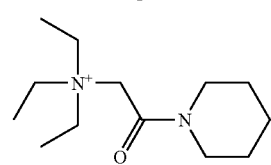

(IX)

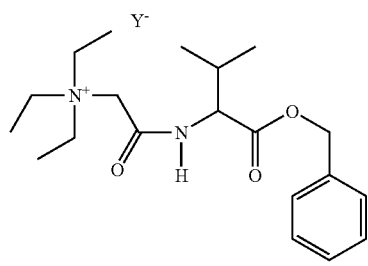
(X)

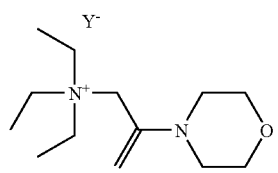
(XI)

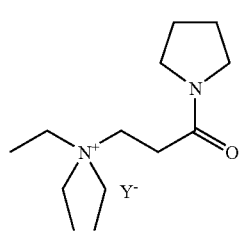
(XII)

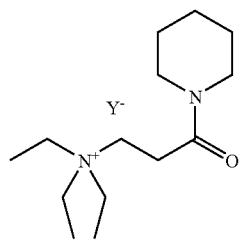
(XIII)

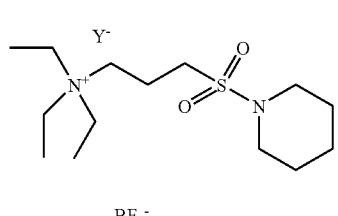
(XIV)

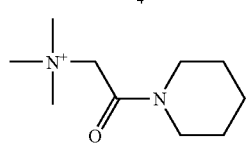
(XV)

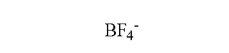
(XVI)

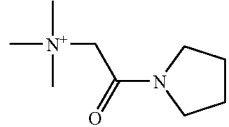
(XVII)

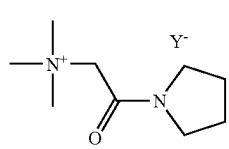

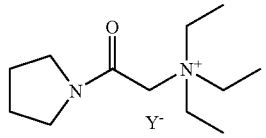
(XVIII)

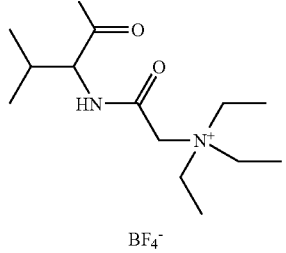
(XIX)

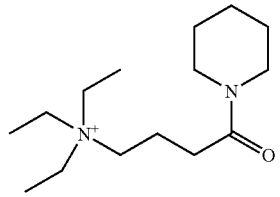
(XX)

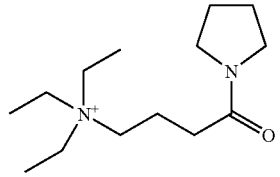
(XXI)

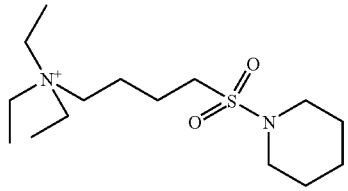
(XXII)

In a third mode of use according to the invention, the organic compound salt includes at least one stereogenic centre, in particular the organic compound salt contains a centre of chirality.

This mode is particularly useful when one or several chiral centres are formed in the course of the electrochemical reaction or in the course of possible subsequent reactions. The diastereomers formed can then easily be separated, and use made of diastereoselective reactions.

In the third use mode according to the invention, the organic compound salt is preferably enantiomerically pure.

"Enantiomerically pure organic compound salt" is intended to mean a chiral organic compound salt consisting essentially of one enantiomer. The enantiomeric excess (ee) is defined as: ee (%)=100 $(x_1-x_2)/(x_1+x_2)$ with $x_1>x_2$; $x_1$ and $x_2$ represent the content of enantiomer 1 or 2 respectively in the mixture.

Generally, an enantiomerically pure organic compound salt with an enantiomeric excess greater than or equal to 99% is used. An enantiomerically pure organic compound salt with an enantiomeric excess greater than or equal to 99.5% is preferred. Particularly preferably, an enantiomerically pure organic compound salt with an enantiomeric excess greater than or equal to 99.9% is used.

The use of an enantiomerically pure organic compound salt makes it possible to obtain organic compounds and in particular electrochemical reaction products exhibiting a high enantiomeric excess.

Specific examples of enantiomerically pure organic compound salts are for example amides of trialkylbetaines of natural or non-natural amino acids such as in particular amides of stachydrine or carnitine. Other amino acid derivatives containing a charged group are mentioned above.

The invention also concerns a process for production of an organic compound comprising
(a) a stage wherein a solution containing an organic compound salt meeting the above description in a solvent is prepared
(b) a stage wherein the solution is subjected to electrolysis in the presence of at least one co-reactant under conditions sufficient to form the product of reaction of the organic compound salt with the co-reactant.

In the process according to the invention, the stage (b) can for example be an electroreduction or an electrooxidation. Preferably, the stage (b) is an electrooxidation.

In the process according to the invention, the stage (b) can be effected in a compartmented or non-compartmented cell.

The electrodes used in the stage (b) must be resistant to the conditions of the electrochemical reaction. Appropriate materials are selected in particular among metals, metal oxides and graphite. Particularly appropriate metals are selected among steel, iron or titanium and in particular among the platinum group metals and their oxides, or electrodes coated with these latter materials. Platinum or rhodium is preferred. An electrode containing platinum is particularly appropriate.

The distance between the electrodes is generally at least 0.2 mm. Often, this distance is at least 0.5 mm. Preferably it is at lest 1 mm. The distance between the electrodes is generally at most 20 mm. Often, this distance is at most 10 mm. Preferably it is at most 5 mm.

In the process according to the invention, the stage (b) is generally effected at a current density greater than or equal to 0.1 A/dm$^2$. Often, the current density is greater than or equal to 1 A/dm$^2$. Preferably, it is greater than or equal to 3 A/dm$^2$ In the process according to the invention, the stage (b) is generally effected at a current density less than or equal to 50 A/dm$^2$. Often, the current density is less than or equal to 30 A/dM$^2$. Preferably, it is less than or equal to 20 A/dm$^2$.

In the process according to the invention, the stage (b) is generally effected at a temperature greater than or equal to −50° C. Often, the temperature is greater than or equal to −20° C. Preferably, it is greater than or equal to 0° C. In the process according to the invention, the stage (b) is generally effected at a temperature less than or equal to 100° C. Often, the temperature is less than or equal to 80° C. Preferably, it is less than or equal to 60° C.

In the process according to the invention, the concentration of organic compound salt in the solution used in the stage (b) is generally greater than or equal to 0.1 moles/l. Often, this concentration is greater than or equal to 0.2 moles/l. Preferably, it is greater than or equal to 0.25 moles/l. In the process according to the invention, the concentration of organic compound salt in the solution used in the stage (b) is generally less than or equal to 3 moles/l. Often, this concentration is less than or equal to 2 moles/l. Preferably, it is less than or equal to 1 mole/l.

Solvents usable in the process according to the invention are generally capable of completely dissolving the desired quantity of organic compound salt at the temperature of the reaction. Examples of usable solvents include water, polar organic solvents and homogeneous mixtures of water with polar organic solvents.

In a first aspect, the solvent is inert under the conditions of the electrochemical reaction. In this case, the solution generally also contains a co-reactant capable of reacting with the organic compound salt having undergone an electron transfer.

In a second aspect, the solvent is itself such a co-reactant. In this aspect, the solvent preferably consists essentially of co-reactant.

It has been found that it is possible to limit the number of constituents of the reaction medium of the process according to the invention to a minimum and to facilitate further the separation and purification of the product of the electrochemical reaction.

The co-reactant capable of being the solvent is often selected among water, alcohols, carboxylic acids and mixtures thereof. The co-reactant is preferably selected among water, methanol, ethanol and acetic acid. Methanol is quite particularly preferred.

Acetic acid is also particularly preferred, especially when the organic compound salt contains an, optionally protected, arginine as described above.

In a quite particularly preferred mode of the process according to the invention, the organic compound salt corresponds to the formula (V) and the co-reactant is methanol.

The process according to the invention can be performed in the virtual absence of the conducting salt. In this case the concentration of conducting salt is-generally less than 0.01 moles/l of solution used. Preferably, the concentration of conducting salt is less than 0.001 moles/l. The solution used can be essentially free from conducting salt.

The product of stage (b) is often a modified organic compound salt. If necessary to obtain the desired final product, further reactions can be performed starting from the modified organic compound salt, for example to eliminate the charged group if necessary, or to modify certain substituents, for example by nucleophilic or electrophilic substitution.

The invention also concerns an organic compound salt corresponding to the formula $$R1R2ZC-T-Q-XY \qquad (XXIII)$$

wherein
X is a charged group as defined above,
Y is a counter-ion as defined above,
Z is a group capable of being substituted,
R1 and R2 mean organic residues as defined above,
T means a group containing a hetero atom selected among N—R4, O and S, NR4 being as defined above, and
Q means a connecting group as defined above, linking the hetero atom and the charged group.

It has been found that the organic compound salt according to the invention is an efficient intermediate for the production of organic substances, presenting substantial advantages as regards its solubility in reaction solvents and allowing easy separation and purification of the products obtained. When the organic compound salt according to the invention is an enantiomerically pure substance, it is an efficient intermediate for asymmetric synthesis.

The substituent Z in particular means a group capable of being replaced by nucleophilic substitution. Such groups can be selected for example among the halogens, in particular chlorine or bromine, esters and alkoxy groups. Esters within the group Z are often selected among the fluorinated esters such as the fluoroacetates, the fluoroalkylsulphonates or the alkly- or aryl-sulphonates. Preferably, the esters are selected among trifluoroacetate, trifluoromethanesulphonate and p-tolylsulphonate. Alkoxy group s often contain 1, 2, 3 or 4 carbon atoms. The methoxy and ethoxy groups are preferred. A methoxy group is quite particularly preferred as the substituent Z.

In a particular embodiment, Z is an O-acetate (OAc) group. It is understood that the combinations and preferences indicated above for the use according to the invention apply equally to the extent that they are applicable, to the organic compound salt according to the invention.

The organic compound salt according to the invention can be obtained by the process according to the invention.

The organic compound salt according to the invention, in particular when Z is methoxy, can be used in substitution reactions, in particular catalysed by acids, in particular Lewis acids, preferably with a silylated reagent such as allyltrimethylsilane or trimethylsilyl cyanide (TMSCN) or with aromatics.

Specific examples of organic compounds obtained from the organic compound salt according to the invention include natural or non-natural amino acids such as proline and β-proline.

The following examples are intended to illustrate the invention, without however limiting it.

EXAMPLE 1

Preparation of 2-(N-pyrrolidine)-N,N,N-triethylethanammonium tetrafluoroborate (1)

3.82 moles of pyrrolidine were added to a solution of 1.92 moles of chloroacetyl chloride in 600 ml of dichloromethane. The temperature was maintained at 0° C. The organic phase was washed with solutions of sodium hydrogen sulphate and sodium carbonate and dried. After evaporation of the solvent, 242 g of N-(2-chloroacetyl)pyrrolidine were obtained. 1.64 moles of this compound were dissolved in 500 ml of toluene and 231 ml of triethylamine were added. This was heated under reflux for 3 hrs and after cooling 311.5 g of product were isolated in the form of a precipitate. 119.07 g of the product obtained were dissolved in 250 ml of boiling dichloromethane in the presence of 7.21 g of $HBF_4$ (54% by weight in diethyl ether) and 112.55 g of 2-N-pyrrolidine)-N,N,N-triethylethanaminium tetrafluoroborate (1) were isolated.

EXAMPLE 2

Preparation of 3-N-piperidine-N,N,N-triethylammoniopropanesulphonamide tetrafluoroborate (2)

By procedures analogous to Example 1, the compound (2) was obtained from piperidine, 3-chloropropylsulphonyl chloride and triethylamine.

EXAMPLES 3 AND 4

Electrochemical Methoxylation

The compound (1) or (2) was dissolved in methanol. This solution was introduced into a non-compartmented cell of volume 150 ml equipped with a cylindrical platinum anode with an internal diameter of 9 mm, an external diameter of 11 mm and an effective length of 27.5 cm, and with a steel cathode. The distance between cathode and anode was 2 mm. The reaction was stopped at the moment when secondary products appeared (selectivity of the order of 100%).

Under the stated conditions, the following results were obtained for the synthesis of 2-(N-2'methoxypyrrolidine)-N,N,N-triethylethanammonium tetrafluoroborate (1a) and 3-N-2'methoxypiperidine-N,N,N-triethylammoniopropane-sulphonamide tetrafluoroboxate (2a) respectively:

| Compound | Concentration (moles/l) | $A/dm^2$ | T ° C. | Chemical yield | Electrochemical yield | Voltage |
|---|---|---|---|---|---|---|
| (1) | 0.74 | 6.7 | 30 | 90% | 65% | 4 V |
| (1) | 0.37 | 20 | 0 | 52% | 68% | 4 V |
| (2) | 0.15 | 6.7 | 30 | 71% | 40% | 4 V |

The methoxylated product (1a) or (2a) respectively was easily isolated by evaporation of the methanol. Its purity was sufficient to allow its use for subsequent reactions.

EXAMPLE 5

1.06 g of (1a) were dissolved in 3 ml of dichloromethane in the presence of 0.9 ml of trimethylsilyl cyanide and 100 μl of SnCl4 at 0° C. and the mixture was stirred. The solution obtained was subjected to hydrolysis with 6 ml of 6N HCl at a temperature of 100° C. It was filtered on an acidic ion exchanger column and eluted with aqueous NH3 (5%). A crude product containing 0.25 g (57%) of proline was isolated.

EXAMPLE 6

In a procedure substantially similar to examples 3 and 4, a solution of 10.15 g (Boc)ArgProOH in 60 ml glacial acetic acid was electrolysed during 3 hours at 25° C. at a current density of 0.025 $A/cm^2$. An HPLC analysis indicated 90% conversion of the starting material: 2.5 mmole of the crude product obtained by evaporation/lyophilisation was reacted at room temperature with 9 mmole allyltrimethylsilane in dichloromethane in the presence of 4 mmole TiCl4. The yield to (Boc)Arg(allyl)pyrrolidine amide was 70%.

The invention claimed is:

1. A method of carrying out an electrooxidation reaction which comprises subjecting a reagent to an electrooxidation wherein said reagent comprises an organic compound salt of general formula (I)

R1R2R3C-T-Q-X Y (I)

wherein

X is a cationic group,

Y is a counter-ion,

R1R2R3C means a substituted carbon atom, capable of reacting in the electroxidation reaction, and R1 and R2 independently are hydrogen atoms, organic residues or R1 and R2 together form organic residues or at least one of R1 or R2 form a ring with the group X, the group Q or the group T, R3 is a group capable of being modified in the course of the electrooxidation reaction, T means an activating group containing a hetero atom selected from the group consisting of N-R4, O and S, wherein R4 is a hydrogen atom or an organic residue, and Q means a connecting group linking the activating group T and the group X.

2. The method according to claim 1, wherein the group X is $NR_3^+$ and R is one or several organic residues.

3. The method according to claim 1, wherein Y is $Br^-$, $Cl^-$, $ClO_4^-$, $BF_4^-$, $PF_6^-$, toluene-sulphonate ($Tos^-$) or benzene-sulphonate ($PhSO_3^-$).

4. The method according to claim 3, wherein Y is a mixture consisting essentially of 90 to 99.5% by weight of at least one ion selected from the group consisting of $ClO_4^-$, $BF_4^-$, $PF_6^{31}$, $^{Tos-}$ and $PhSO_3^-$ and 0.5 to 10% by weight of $Cl^-$.

5. The method according to claim 1, wherein the group Q is a linear or branched alkylene or cyclo-alkene group, optionally substituted with a functional group and optionally linked to the group T by a functional selected from the group consisting of —(C=O)—, —N—(C=O)—, —O—(C=O)—, —(S=O)—, —N—(S=O)—, —$SO_2$—, —N—$SO_2$—, —(C=S)— and —N—(C=S)—.

6. The method according to claim 1, wherein R3 is hydrogen.

7. The method according to claim 1, wherein the organic compound salt comprises at least one stereogenic center and is enantiomerically pure.

8. The method according to claim 1, wherein the organic compound salt corresponds to the formula (I)

$$R1R2R3C\text{-}T\text{-}Q\text{-}X\ Y \qquad (I)$$

wherein the group Q is a linear or branched alkylene group, optionally substituted with a functional group and linked to the group T by a functional selected from the group consisting of —(C=O)—, —N—(C=O)—, —O—(C=O)— and —$SO_2$— and T in the formula (I) is NR4 and X in the formula (I) is $NR_3^+$ and R is an organic residue.

9. The method according to claim 1, wherein said organic compound salt is provided as a solution in a solvent.

10. The method according to claim 9, wherein said solvent is inert under conditions of said electrooxidation reaction.

11. The method according to claim 10, wherein said method further comprises reacting said reagent comprising said organic compound salt with at least one co-reactant capable of reacting with said organic compound salt.

12. The method according to claim 9, wherein said solvent is itself a co-reactant capable of reacting with said organic compound salt.

13. The method according to claim 1, comprising the electrooxidation of said organic compound salt, wherein said electrooxidation is carried out at a current density of from 0.1 to 50 $A/dm^2$.

14. The method according to claim 13, wherein said electrooxidation is carried out at a temperature of from −50 to 100° C.

* * * * *